United States Patent [19]
Audenaert et al.

[11] Patent Number: 5,817,249
[45] Date of Patent: Oct. 6, 1998

[54] CARBODIIMIDE COMPOUND AND WATER REPELLENT COMPOSITIONS

[75] Inventors: Frans A. G. Audenaert, Kaprijke; Hugo R. Lens, Boechout, both of Belgium

[73] Assignee: Minnesota Minning and Manufacturing Company, St. Paul, Minn.

[21] Appl. No.: 546,886

[22] Filed: Oct. 23, 1995

[30] Foreign Application Priority Data

Nov. 24, 1994 [EP] European Pat. Off. ............. 94118500

[51] Int. Cl.⁶ ................... D06M 15/256; D06M 15/564
[52] U.S. Cl. ................ 252/8.61; 252/8.81; 252/8.91; 524/805; 524/840; 524/839; 525/123; 525/129; 525/130; 525/131; 427/212; 427/216; 427/222
[58] Field of Search ................ 525/194, 123, 525/129, 130, 131; 252/8.61, 8.81, 8.91; 524/805, 839, 840; 427/212, 216, 221, 222

[56] References Cited

U.S. PATENT DOCUMENTS

| | | |
|---|---|---|
| 2,941,983 | 6/1960 | Smeltz . |
| 2,941,988 | 6/1960 | Wolf . |
| 3,341,497 | 9/1967 | Sherman et al. . |
| 3,420,697 | 1/1969 | Sweeney et al. . |
| 3,445,491 | 5/1969 | Pacini . |
| 3,470,124 | 9/1969 | Van Eygen . |
| 3,544,537 | 12/1970 | Brace . |
| 3,546,187 | 12/1970 | Tandy . |
| 3,862,989 | 1/1975 | Hansen . |
| 3,896,251 | 7/1975 | Landucci . |
| 3,993,833 | 11/1976 | Esmay ..................... 428/311 |
| 4,054,592 | 10/1977 | Dear et al. . |
| 4,067,945 | 1/1978 | Elmer . |
| 4,215,205 | 7/1980 | Landucci . |
| 4,426,466 | 1/1984 | Schwartz . |
| 4,468,527 | 8/1984 | Patel . |
| 4,477,498 | 10/1984 | Deine et al. . |
| 4,540,497 | 9/1985 | Chang et al. . |
| 4,560,487 | 12/1985 | Brinkley ..................... 252/8.75 |
| 4,566,981 | 1/1986 | Howells . |
| 4,834,764 | 5/1989 | Deiner et al. . |
| 5,132,028 | 7/1992 | Nagase et al. . |
| 5,164,252 | 11/1992 | Henning et al. . |
| 5,498,747 | 3/1996 | Pohl et al. . |

FOREIGN PATENT DOCUMENTS 436 327 A1  7/1991  European Pat. Off. .

OTHER PUBLICATIONS

K Wagner et al., "α,ω–Diisocyanatocarboniimides, –Polycarboniimides, and Their Derivatives" *Angew. Chem.* Int. Ed. Engl., vol. 20, pp. 819–830 (1981).

S.R. Sandler et al. *Org. Functional Group Prep.*, vol. 2, pp. 205–222 (1971).

A Williams et al., "Carbodiimide Chemistry: Recent Advances," *Chem. Rev.*, vol. 81, pp. 589–636 (1981).

Campbell, T.W. and Smeltz, K.C., "Carbodiimides IV. High Polymers Containing the Carbodiimide Repeat Unit," *J. of Org. Chem.*, vol. 28, pp. 2069–2075 (1963).

*Primary Examiner*—Jeff Mullis
*Attorney, Agent, or Firm*—Lucy C. Weiss

[57] ABSTRACT

Invention relates to new carbodiimide compound obtainable from reaction mixture comprising an isocyanate compound and a monofunctional alcohol in a non-reactive solvent in the presence of a suitable catalyst, characterized in that the isocyanate compound and the monofunctional alcohol, except for the hydroxy group, are free from isocyanate reactive hydrogen atoms and the monofunctional alcohol is a branched aliphatic alcohol containing at least 8 carbon atoms, and to compositions comprising a fluorochemical oil and water repellent agent and said carbodiimide compound.

9 Claims, No Drawings

5,817,249

CARBODIIMIDE COMPOUND AND WATER REPELLENT COMPOSITIONS

TECHNICAL FIELD

This invention relates to a new carbodiimide compound and to compositions comprising a fluorochemical oil and water repellent agent and said carbodiimide compound. This invention, in another aspect, relates to a method for imparting oil and water repellent properties to fibrous substrates and other materials and to the resulting treated substrates.

BACKGROUND

The use of various fluorochemical compositions on fibers and fibrous substrates, such as textiles, paper and leather, to impart oil and water repellency is known. See for example, Banks, Ed., *Organofluorine Chemicals and Their Industrial Applications*, Ellis Horwood Ltd., Chichester, England, 1979, pp. 226–234. Such fluorochemical compositions include, for example, fluorochemical guanidines (U.S. Pat. No. 4,540,497), compositions of cationic and non-ionic fluorochemicals (U.S. Pat. No. 4,566,981), compositions containing fluorochemical carboxylic acid and epoxidic cationic resin (U.S. Pat. No. 4,426,466), and fluoroaliphatic alcohols (U.S. Pat. No. 4,468,527).

Additives have been employed to assist in the oil and water repellency of fluorochemical treating agents. U.S. Pat. No. 4,215,205 teaches that durable launderable and dry-cleanable repellency to water and oil is conferred on fabrics consisting of hydrophobic synthetic fibers by application of a blend of a fluoroaliphatic vinyl polymer and a carbodiimide.

Fluorochemicals are generally expensive. Therefore, hydrocarbon additives, also called extenders, have been developed in order to reduce cost. Modified synthetic resins, waxes, melamines, paraffin emulsions, and similar products have been used as extenders.

U.S. Pat. No. 4,834,764 describes a process for obtaining wash- and cleaning-resistant textile finishes by impregnating with reactive perfluoroalkyl-containing (co)polymers and/or precondensates in aqueous dispersion and heating, wherein the dispersions have NCO-containing compounds which have a molecular weight of at least 450 and/or contain a diphenylmethane-based polyisocyanate mixture in blocked form.

U.S. Pat. No. 5,164,252 teaches that phobicity effects of high quality and permanence are obtained on textile materials of the most diverse types if they are finished with combinations of A) a polymer containing perfluoroalkyl groups and B) a cationically modified polyurethane.

U.S. Pat. No. 5,132,028 discloses compositions for imparting water and oil repellency to fabrics such as silk, said compositions containing a fluorochemical-type, water and oil repellent agent, a carbodiimide, and at least one component selected from the group consisting of plasticizer, metal alcoholate or ester, zirconium salt, alkylketene dimer, aziridine, and alkenyl succinic anhydride.

DISCLOSURE OF INVENTION

It is an object of the present invention to provide a new carbodiimide compound which can be used as an extender. It is a further object of the present invention to provide a water and oil repellency imparting composition which has a low fluorine content. Furthermore it is an object of the invention to provide a composition and a process for conferring both static and especially dynamic water resistance onto fibers, particularly to cellulosic type fibers.

The present invention provides a carbodiimide compound obtainable from a reaction mixture comprising an isocyanate compound and a monofunctional alcohol in a non-reactive solvent in the presence of a suitable catalyst, characterized in that the isocyanate compound and the monofunctional alcohol, except for the hydroxy group, are free from isocyanate reactive hydrogen atoms and the monofunctional alcohol is a branched aliphatic alcohol containing at least 8 carbon atoms.

In a further aspect, the present invention provides a water repellent composition comprising (A) a fluorochemical oil and water repellent agent; and (B) said carbodiimide as extender. The treatment composition of the invention is characterized by a low overall fluorine content. The invention provides an oil and water repellent treatment composition suitable for synthetic and especially for cellulosic fibers and substrates. The treatment provides a gentle touch to the fibers and substrates and displays a high durability to cleaning. Said carbodiimides are amorphous in nature, are essentially fluorine free and contain terminal portions which are branched aliphatic moieties, preferably derived from branched higher alcohols.

In another aspect, the present invention provides a method for imparting oil- and water-repellent properties to a fibrous substrate comprising the steps of (1) applying to the surface of a fibrous substrate an amount of the water repellent composition just described, wherein said fluorochemical agent and said carbodiimide extender are present in a total combined amount of 0.01% to 5% by weight based on the weight of the fibrous substrate, and (2) heating the treated substrate from step 1 at a temperature and for a time sufficient to cure the treated substrate. In another aspect, this invention provides substrates treated with the fluorochemical composition of this invention.

The amorphous carbodiimides useful in the compositions of this invention act as excellent extenders in treatment of fibrous substrates, thus allowing more efficient use of the more expensive fluorochemical agent.

DETAILED DESCRIPTION

In general, fluorochemical agents useful in the invention include any of the known fluoroaliphatic radical-containing agents useful for the treatment of fabrics to obtain oil and water repellency. Fluorochemical radical-containing agents include condensation polymers such as polyesters, polyamides or polyepoxides and vinyl polymers such as polyacrylates, polymethacrylates or polyvinyl ethers. Such known agents include, for example, those described in U.S. Pat. No. 3,546,187; U.S. Pat. No. 3,544,537; U.S. Pat. No. 3,470,124; U.S. Pat. No. 3,445,491; U.S. Pat. No. 3,341,497 and U.S. Pat. No. 3,420,697.

Further examples of such fluoroaliphatic radical-containing water and oil repellency imparting agents include those formed by the reaction of perfluoroaliphatic glycols or thioglycols with diisocyanates to provide perfluoroaliphatic group-bearing polyurethanes. These products are normally applied as aqueous dispersions for fibre treatment. Such reaction products are described, for example, in U.S. Pat. No. 4,054,592. Another group of compounds which can be used are fluoroaliphatic radical-containing N-methylolcondensation products. These compounds are described in U.S. Pat. No. 4,477,498. Further examples include fluoroaliphatic radical containing polycarbodiimides which can be obtained by, for example, reaction of perfluoroaliphatic sulfonamido alkanols with polyisocyanates in the presence of suitable catalysts.

The fluorochemical compound is preferably a copolymer of one or more fluoroaliphatic radical-containing acrylate or methacrylate monomers, and one or more fluorine-free (or hydrocarbon) terminally ethylenically-unsaturated comonomers. Classes of the fluorochemical monomers can be represented by the formulas

$R_fR^1OCOC(R^2)=CH_2$ and $R_fSO_2N(R^3)R^4OCOC(R^2)=CH_2$
where $R_f$ is a fluoroaliphatic radical;

$R^1$ is an alkylene with 1 to 10 carbon atoms, e.g. methylene or ethylene, or $-CH_2CH(OR)CH_2-$, in which R is hydrogen or $COCH_3$;

$R^2$ is hydrogen or methyl;

$R^3$ is hydrogen or an alkyl with 1 to 20, preferably 1 to 10 carbon atoms, e.g. methyl or ethyl; and $R^4$ is an alkylene with 1 to 20, preferably 1 to 10 carbon atoms, e.g. methylene or ethylene.

The fluoroaliphatic radical, called $R_f$ for brevity, is a fluorinated, stable, inert, preferably saturated, non-polar, monovalent aliphatic radical. It can be straight chain, branched chain, cyclic or combinations thereof It can contain heteroatoms, bonded only to carbon atoms, such as oxygen, divalent or hexavalent sulfur, or nitrogen. $R_f$ is preferably a fully-fluorinated radical, but hydrogen or chlorine atoms can be present as substituents if not more than one atom of either is present for every two carbon atoms. The $R_f$ radical has at least 3 carbon atoms, preferably 3 to 14 carbon atoms, and preferably contains about 40% to about 80% fluorine by weight, more preferably about 50% to about 78% fluorine by weight. The terminal portion of the $R_f$ radical is a perfluorinated moiety, which will preferably contain at least 7 fluorine atoms, e.g., $CF_3CF_2CF_2-$, $(CF_3)_2CF-$, $F_5SCF_2-$. The preferred $R_f$ radicals are fully or substantially fluorinated and are preferably those perfluorinated aliphatic radicals of the formula $C_nF_{2n+1}-$ where n is 3 to 14.

Representative examples of fluorochemical monomers include:

$CF_3(CF_2)_4CH_2OCOC(CH_3)=CH_2$

$CF_3(CF_2)_6(CH_2)_2OCOC(CH_3)=CH_2$

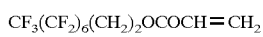
$CF_3(CF_2)_6(CH_2)_2OCOCH=CH_2$

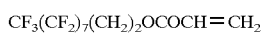
$CF_3(CF_2)_7(CH_2)_2OCOCH=CH_2$

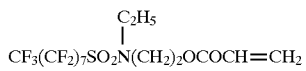
$CF_3(CF_2)_7SO_2N(C_2H_5)(CH_2)_2OCOCH=CH_2$

$CF_3CF_2(CF_2CF_2)_{2-8}CH_2CH_2OCOCH=CH_2$

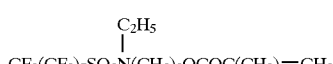
$CF_3(CF_2)_7SO_2N(C_2H_5)(CH_2)_2OCOC(CH_3)=CH_2$

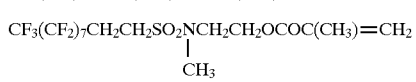
$CF_3(CF_2)_7CH_2CH_2SO_2N(CH_3)CH_2CH_2OCOC(CH_3)=CH_2$

Preferred co-monomers which can be copolymerized with the above-described fluoroaliphatic radical-containing monomers include those selected from the group consisting of octadecylmethacryate, 1,4-butanediol diacrylate, laurylmethacrylate, butylacrylate, N-methylol acrylamide, isobutylmethacrylate, ethylhexyl acrylate, ethylhexyl methacrylate, vinylchloride and vinylidene chloride. The relative weight ratio of the fluoroaliphatic monomer(s) to the hydrocarbon co-monomer(s) can vary as is known in the art.

The carbodiimide extenders of this invention are amorphous in nature with a typical glass transition temperature between −30° C. and +80° C. and are represented by the general formulas (I)–(III):

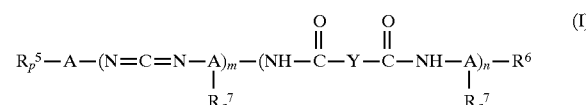

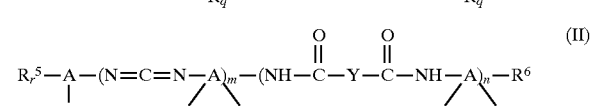

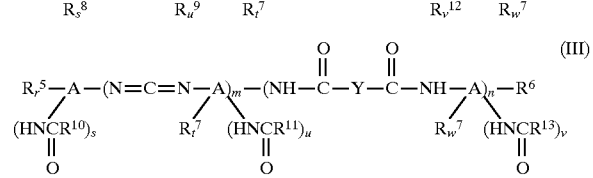

wherein: n is 0 or an integer from 1 to 4; m is an integer from 1 to 20, preferably from 1 to 10. p and r+s are 1, 2 or 3, respectively for di-, tri- or tetraisocyanates; q, u+t and v+w are 0, 1 or 2 respectively for di-, tri- or tetraisocyanates.

Y is a divalent linking group obtained by removing active hydrogens from a poly(oxy)alkylene diol, tertiary amino group containing diol or quaternary ammonium group containing diol.

The linking group A is an organic residue obtained by removing all isocyanate groups from an isocyanate compound. The A-groups may be the same or different. Some of the A-groups may be, for example trivalent or tetravalent derived from triisocyanates or tetraisocyanates such as polymethylene polyphenyl isocyanates. When A is polyvalent, branched or crosslinked polycarbodiimides can result. Different A-groups may be used together to give slight branching in order to modify properties. Substituents may be present in A provided they contain no isocyanate-reactive hydrogen atoms; that is, groups such as —OH are normally excluded. Unsubstituted organic linking groups are preferred. Preferred groups A are for example

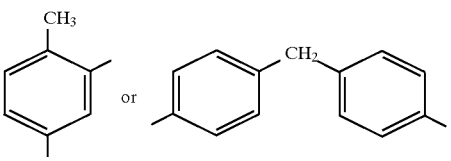

The terminal and pending groups $R^5$, $R^6$ and $R^7$ are independently monovalent organic radicals free from isocyanate reactive hydrogen atoms and containing a branched aliphatic terminal moiety of at least 8 carbon atoms. More preferably at least 8 to 60 carbon atoms, especially 14 to 60 carbon atoms. The branching can be random, but preferably it is alpha-branching.

In a preferred embodiment, the $R^5$, $R^6$ and $R^7$ groups are each independently a group of the general formula

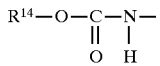

wherein $R^{14}$ is a branched $C_{8-60}$ alkyl group.

Preferably, $R^5$, $R^6$, $R^7$ and A are essentially free from fluorine (i.e. do not contain more than 0.3% by weight of fluorine).

The terminal groups $R^8$, $R^9$ and $R^{12}$ are monovalent organic radicals containing a poly(oxy)alkylene moiety and/ or tertiary amino group and/or quaternary ammonium function. Useful examples for $R^8$, $R^9$ and $R^{12}$ include

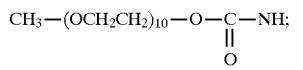

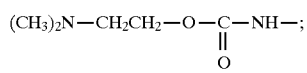

and

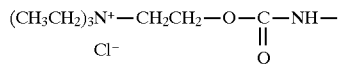

The terminal groups $R^{10}$, $R^{11}$ and $R^{13}$ are monovalent organic radicals obtained by removing an active hydrogen from a poly(oxy)alkylene diol monoalkylether, tertiary amino group containing alcohol or quaternary ammonium group containing alcohol. Useful examples of $R^{10}$, $R^{11}$ and $R^{13}$ include e.g.

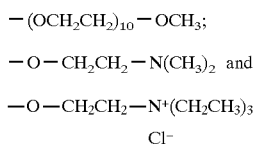

Carbodiimides can be obtained by condensation of isocyanates in the presence of suitable catalysts as described, for example by K Wagner et al., Angew. Chem. Int. Ed. Engl., vol 20, p 819–830 (1981); by S. R. Sandler et al., Org. Functional Group Prep., vol 2, p 205–222 (1971) and by A Williams et al., Chem. Rev., vol 81, p 589–636 (1981). The preparation of urethane containing or urethane terminated polycarbodiimides has been described in e.g. U.S. Pat. No. 2,941,983 and by T. W. Campbell et al. in J. Org. Chem., 28, 2069 (1963).

The carbodiimides of the invention are usually made in a two step reaction starting from diisocyanates or multifunctional isocyanates and monofunctional alcohols in a non-reactive solvent such as methyl isobutyl ketone, at a concentration of about 40% of dissolved materials. The reaction mixture is prepared so that water is removed before addition of isocyanates, and is heated until the urethane reaction is complete. After completion of the urethane reaction, in a second step, the carbodiimide is formed after adding a phospholine oxide or other suitable catalyst. Representative examples of suitable catalysts are described in e.g. U.S. Pat. No. 2,941,988, U.S. Pat. No. 3,862,989 and U.S. Pat. No. 3,896,251. Examples include 1-ethyl- 3-phospholine, 1-ethyl-3-methyl-3-phospholine-1-oxide, 1-ethyl-3-methyl-3-phospholine-1-sulfide, 1-ethyl-3-methyl-phospholidine, 1-ethyl-3-methyl-phospholidine-1-oxide, 3-methyl-1-phenyl-3-phospholine-1-oxide and bicyclic terpene alkyl or hydrocarbyl aryl phosphine oxide or camphene phenyl phosphine oxide.

The particular amount of catalyst used will depend to a large extent on the reactivity of the catalyst itself and the organic polyisocyanate being used. A concentration range of 0.1–10 parts of catalyst per 100 parts of organic diisocyanate is suitable. About 0.5–2.0 parts of catalyst is satisfactory when aromatic diisocyanates are used. The final reaction mixture can be dispersed in water and further diluted with water before application.

In order to improve the stability of the emulsions prepared from the carbodiimides of the present invention, poly(oxy) alkylene and/or tertiary or quaternary amino-group containing reactants with at least one active hydrogen may be incorporated into the carbodiimide. Therefore, in a further embodiment of the present invention the reaction mixture used for the preparation of the carbodiimides comprises an amount of a poly(oxy)alkylene and/or a tertiary or quaternary amino group containing reactant with at least one active hydrogen.

Poly(oxy)alkylene reactants with at least one active hydrogen used in the preparation of carbodiimides are normally liquid or low melting solids. They can be represented by the general formula:

$$H-(R')_n-OR''$$

wherein

R' is an oxyalkylene group with 2 to 4 carbon atoms; n is an integer of at least 4, generally 10 to 75 and can be as high as 100 or higher R'' is hydrogen or an alkyl group having 1 to 4 carbon atoms.

Said R' group is an oxyalkylene group having 2 to 4 carbon atoms, such as —$OCH_2CH_2$—, —$OCH_2CH_2CH_2$—, —$OCH(CH_3)CH_2$—and —$OCH(CH_3)CH(CH_3)$—. Preferably the oxyalkylene units in said poly(oxyalkylene) are the same, as in poly(oxypropylene), or are present as two types of groups, as in a straight or branched chain or randomly distributed oxyethylene and oxypropylene units, or as in a straight or branched chain of blocks of oxyethylene units and blocks of oxypropylene units. Poly(oxy)alkylene reactants having amino functionality can be used as well.

The molecular weight of the poly(oxyalkylene) reactant can be as low as 200 but preferred is about 300 to 4000 or higher. When used, the poly(oxyalkylene) reactant can be present up to about 20% by weight based on the total weight of the carbodiimide. The poly(oxyalkylene)radicals in the carbodiimide can be the same or different, and they can be pendent.

Representative active hydrogen-group containing tertiary organo amine reactants useful in the preparation of carbodiimides include 2-dimethylaminoethanol, 2-diethylaminoethanol, 2-diisopropylaminoethanol, N-methyldiethanolamine, triethanolamine, 1-methyl-3-pyrrolidinol, 2(2-hydroxyethyl)pyridine, N(2-hydroxyethyl) morpholine, 1,4-bis(2-hydroxypropyl)-piperazine, 1,1-dimethyl-4-dimethylamino-n-butanol, N(2-hydroxyethyl)-N-methylaniline, 2-dimethylaminoethanethiol, N,N-bis(2-mercaptoethyl)methylamine, 4-diethylamino-1-methyl-n-butanol, 1 -dimethylamino-2propanol, 3-dimethylamino-1-propanol, 3-dimethylamino-2hydroxy-n-propanol and mixtures thereof.

The amino-group containing carbodiimides can be converted to quaternary compounds using alkylating agents or acids. Quaternizing alkylating agents and acids useful in this invention include methyl iodide, methyl bromide, allyl chloride, benzyl chloride, diethylsulfate, dimethylsulfate, epichlorohydrin, hydrochloric acid, acetic acid, glycolic acid and the like. When used, the reactant containing aminofunctional groups will be present up to about 5% by weight based on the total weight of reactants.

The water repellent compositions of the invention can be prepared by blending emulsions of fluorochemical oil and water repellent agent and carbodiimide, together with any desired compatible additives. Alternatively, the fluorochemical agent and the carbodiimide can be prepared in solution and the solutions blended, diluted if necessary and applied to the substrate.

In order to improve fixing of the composition of the invention to a substrate, it is sometimes advantageous to include in the dispersion certain additives, polymers, thermo-condensable products and catalysts capable of promoting interaction with the substrate. Among these are the condensates or precondensates of urea or melamine with formaldehyde (sometimes referred to herein as resins) and glyoxal resins. Particular suitable additives and amounts thereof can be selected by those skilled in the art.

The amount of the treating composition applied to a substrate in accordance with this invention is chosen so that sufficiently high or desirable water and oil repellencies are imparted to the substrate surface, said amount usually being such that 0.01% to 5% by weight, preferably 0.05% to 2% by weight, based on the weight of the substrate, of water repellent composition (fluorochemical and carbodiimide) is present on the treated substrate. The amount which is sufficient to impart desired repellency can be determined empirically and can be increased as necessary or desired.

The carbodiimide extender is present in an amount sufficient to improve the fluorine efficiency of the fluorochemical agent. "Improvement in fluorine efficiency" as used herein designates that improved or equal repellency properties are obtained when part of the fluorochemical treating agent, preferably 10 to 50% by weight of fluorochemical treating agent, is replaced by the carbodiimide. Generally, the carbodiimide is present in an amount of about 5 to about 500, preferably about 10 to about 200, and most preferably about 25 to about 100 parts by weight based on 100 parts by weight of the fluorochemical treating agent.

The composition of this invention can be applied using conventional application methods and can be used as an aqueous dispersion or alternatively it can be used as a treatment composition in solvent. A dispersion will generally contain water, an amount of composition effective to provide repellent properties to a substrate treated therewith, and a surfactant in an amount effective to stabilize the dispersion. Water is preferably present in an amount of about 70 to about 20000 parts by weight based on 100 parts by weight of the composition of the invention. The surfactant is preferably present in an amount of about 1 to about 25 parts by weight, preferably about 5 to about 10 parts by weight, based on 100 parts by weight of the inventive composition. Conventional cationic, nonionic, anionic, and zwitterionic surfactants are suitable.

In order to effect treatment of a substrate, the substrate can be immersed in the dispersion and agitated until it is saturated. The saturated substrate can then be run through a padder/roller to remove excess dispersion, dried in an oven at a relatively low temperature (eg., 70° C.) for a time sufficient to remove the dispersion medium (e.g.; water, ethylene glycol, or a mixture thereof), and cured at a temperature and for a time sufficient to provide a cured treated substrate. This curing process can be carried out at temperatures between about 110° C. and about 190° C. depending on the particular system or application method used. In general, a temperature of about 150° C. for a period of about 20 seconds to 10 minutes, preferably 3 to 5 minutes, is suitable. The cured treated substrate can be cooled to room temperature and used as desired, eg. incorporated or fashioned into a garment such as rainwear.

The substrates treated by the water and oil repellency imparting composition of this invention are not especially limited and include, e.g., textile fabrics, fibres, non-wovens, leather, paper, carpet, plastic, wood, metal, glass, concrete and stone. Preferred are textile fabrics, fibres and non-wovens, especially of the cellulosic type, such as eg. rayon, cotton, linen.

Formulation and Treatment Procedure

Treatment baths were formulated containing a defined amount of the fluorochemical treatment agent and the carbodiimide. Treatments were applied to the test substrates by padding at a concentration of 0.3% solids (based on fabric weight and indicated as SOF (solids on fabric)) unless otherwise indicated, and drying and curing at 150° C. for 3 minutes. Substrates used for the evaluation of treatments of this invention are all commercially available and are listed below:

PES/CO: Grey polyester/cotton 65/35, style No. 2681, obtained through Utexbel N.V., Ghent, BELGIUM 100% Cotton: bleached, mercerized cotton poplin, style No. 407, purchased from Testfabrics, Inc., USA 100% Polyamide: Polyamide microfiber, obtained from Sofinal BELGIUM 100% Polyester: Polyester microfiber, obtained from Sofinal BELGIUM Respective data of water and oil repellency shown in the Examples and Comparative Examples are based on the following methods of measurement and evaluation criteria.

Bundesmann Test

The impregnating effect of rain on treated substrates is determined using the Bundesmann Test Method (DIN 53888). In this test, the treated substrates are subjected to a simulated rainfall, while the back of the substrate is being rubbed. The appearance of the upper exposed surface is checked visually after 1, 5 and 10 minutes and is given a rating between 1 (complete surface wetting) and 5 (no water remains on the surface). Besides the observation of the wetting pattern also the water absorption (% ABS) and penetration after 10 min rain test can be quantitatively measured. Well treated samples give low absorption and penetration results.

Spray Rating (SR)

The spray rating of a treated substrate is a value indicative of the dynamic repellency of the treated substrate to water that impinges on the treated substrate. The repellency is measured by Standard Test Number 22, published in the 1985 Technical Manual and Yearbook of the American Association of Textile Chemists and Colorists (AATCC), and is expressed in terms of 'spray rating' of the tested substrate. The spray rating is obtained by spraying 250 ml water on the substrate from a distance of 15 cm. The wetting pattern is visually rated:using a 0 to 100 scale, where 0 means complete wetting and 100 means no wetting at all.

Oil Repellency (OR)

The oil repellency of a treated substrate is measured by the American Association of Textile Chemists and Colorists (AATCC) Standard Test Method No. 118–1983, which test is based on the resistance of a treated substrate to penetration by oils of varying surface tensions. Treated substrates resistant only to Nujol®, mineral oil (the least penetrating of the test oils) are given a rating of 1, whereas treated substrates resistant to heptane (the most penetrating of the test oils) are given a rating of 8. Other intermediate values are determined by use of other pure oils or mixtures of oils, as shown in the following table.

| Standard Test Liquids | |
|---|---|
| AATC Oil Repellency Rating Number | Compositions |
| 1 | Nujol ® |
| 2 | Nujol ® /n-hexadecane 65/35 |

-continued

| AATC Oil Repellency Rating Number | Compositions |
|---|---|
| 3 | n-Hexadecane |
| 4 | n-Tetradecane |
| 5 | n-Dodecane |
| 6 | n-Decane |
| 7 | n-Octane |
| 8 | n-Heptane |

Standard Test Liquids

Laundering Procedure

The procedure set forth below was used to prepare treated substrate samples designated in the examples below as "5 Launderings (5L)".

A 230 g sample of generally square, 400 cm² to about 900 cm² sheets of treated substrate was placed in a washing machine along with a ballast sample (1.9 kg of 8 oz fabric in the form of generally square, hemmed 8100 cm² sheets). Conventional detergent (Tide, 46 g) is added and the washer is filled to high water level with hot water (40° C. ±3° C.). The substrate and ballast load is washed five times (no drying in between the cycles) using a 12-minute normal wash cycle followed by five rinse cycles and centrifuging. The dry substrate is pressed using a hand iron set at the temperature recommended for the particular substrate fabric.

Abbreviations

The following abbreviations and trade names are used in the examples:

MeFOSEA: $C_8F_{17}SO_2N(CH_3)CH_2CH_2OC(O)CH=CH_2$
MeFOSEMA: $C_8F_{17}SO_2N(CH_3)CH_2CH_2OC(O)C(CH_3)=CH_2$
EHMA: $n-C_4H_9CH(C_2H_5)CH_2OC(O)C(CH_3)=CH_2$
N-MAM: $HOCH_2NHC(O)CH=CH_2$ (48 wt% aqueous solution)
MDI: 4,4'methylene diphenyl diisocyanate (available as Desmodur 44 MS from Bayer, Leverkusen, Germany)
TDI: toluene diisocyanate (available as Desmodur T100 from Bayer, Leverkusen, Germany)
Voranate M220: polymethylene polyphenyl isocyanate, available from Dow Chemical, Terneuzen, The Netherlands
Guerbitol-16: 2-alkylalkanols, known as Guerbet alcohols,
Guerbitol-18: the number indicating the average chain
Guerbitol-20: length; available from Henkel, Dusseldorf, Germany
Isofol-14T: 2-alkylalkanols
Isofol-16: the number indicating the
Isofol-18T: average chain length;
Isofol-20: available from Condea, Brunsbuttel,
Isofol-24: Germany
Prisorine 3515: methyl branched isostearylalcohol available from Unichema Chemie, Gouda, The Netherlands
Jeffamine 715: monofunctional polyoxyalkyleneamine with an average molecular weight (Mw) of 715, available from Huntsman, Tex., USA
MPEG 750: monofunctional methoxyterminated polyethylene-
MPEG 350: glycols with an average Molecular weight of 750 and 350 respectively, available from Acros Chimica, Geel, Belgium
DEAE: N-diethylaminoethanol, available from Acros Chemica, Geel, Belgium
Ethoquad 18/25: Methyl polyoxyethylene(15)octadecyl ammonium chloride, available from Akzo, Littleborough, UK
Ethoquad HT-25: Methyl polyoxyethylene (15) hydrogenated tallow ammonium chloride, available from Akzo, Littleborough, UK
Arquad T-50: tallow trimethyl ammonium chloride, available from Akzo, Littleborough, UK
Arquad 2HT-75: dimethyl-dihydrogenated tallow ammonium chloride; available from Akzo, Littleborough, UK
Atpol E5721: alkylethoxylate, available from ICI, Wilton, UK
Atlas G1281: polyoxyethylene fatty glyceride, available from ICI, Wilton, UK
Marlowet 5401: polyethoxylated amine salt, available from Hülls, Marl, Germany All parts, ratios, percentages, etc. in the following examples and the rest of the specification, are by weight unless otherwise noted.

Preparation of the Carbodiimide Compounds

Several hydrocarbon carbodiimides (HCD) as given in table 1 have been prepared according to the general procedure as described for the synthesis of the carbodiimide made from MDI/Guerbitol-18 in a molar ratio of 2/1. The carbodiimides are emulsified before addition to the fluorochemical composition.

A. Preparation of Hydrocarbon Carbodiimide

The hydrocarbon carbodiimides are prepared in two steps. First a urethane reaction is carried out between the branched alcohol and an isocyanate. In a second step, the carbodiimide is formed.

1. For the first reaction, a 1 liter 3-necked glass reaction flask, equipped with a thermometer, a Dean-Stark condenser, a nitrogen inlet tube, a mechanical stirrer, and an electric heating mantle is charged with 0.4 mole Guerbitol-18 in methyl isobutyl ketone (MIBK) at a concentration of 22% by weight, under an atmosphere of dry nitrogen. The solution is heated until reflux and 100 g distillate is removed via the Dean Stark condenser. The Dean Stark condenser is subsequently replaced by a normal reflux condenser. The reaction mixture is cooled to 55° C., after which 0.8 mole of MDI is added. The reaction mixture is heated to 60° C. and stirred until a clear solution is obtained. 40 mg dibutyl tin dilaurate catalyst (available from Air Products Company) is added and the reaction mixture is stirred for 3 hours at 80° C.

2. In a second step, the carbodiimide is formed. A camphene phenyl phosphine oxide catalyst is added to the mixture (2% based on MDI solids). The reaction is then run for 10 hours at 100° C. at which time the isocyanate functional groups have been fully converted into carbodiimide functions as shown by FTIR spectroscopy. The final product is a slightly hazy solution.

B. Emulsification

The carbodiimides prepared can be emulsified using different surfactants or mixtures of surfactants, following the general procedure as described for the Marlowet 5401 surfactant. A solution of 126 g deionized water and 4 g Marlowet 5401 surfactant is heated to 75° C. in a 500 ml beaker. 100 g carbodiimide solution (50% solids) as prepared under A is heated to 75° C. and added to the surfactant solution while stirring vigorously. This preemulsion is converted into a stable milky dispersion using a Branson 250 Sonifier. The MIBK solvent can be distilled off with a Buchi rotavapor using waterjet vacuum. The carbodimides given in table 1 have been emulsified according to this general method.

The kind and amount of surfactant may be varied, depending on the carbodiimide used, especially the carbodiimides that contain poly(oxyalkylene) or amine groups can be emulsified with lower level of or no surfactant added. Depending on the solubility of the surfactant, the surfactant can be added to the aqueous or to the organic phase.

TABLE 1

Structure of carbodiimides

| Abbrev. | Isocyanate | Alcohol | Poly(oxy)alkylene or amino-group containing reactant | Molar Ratio |
|---|---|---|---|---|
| HCD-1 | MDI | Prisorine 3515 | | 3/2 |
| HCD-2 | MDI | Prisorine 3515 | | 2/1 |
| HCD-3 | MDI | Guerbitol-16 | | 3/2 |
| HCD-4 | MDI | Guerbitol-18 | | 3/2 |
| HCD-5 | MDI | Guerbitol-18 | | 2/1 |
| HCD-6 | MDI | Guerbitol-20 | | 3/2 |
| HCD-7 | MDI | Guerbitol-20 | | 2/1 |
| HCD-8 | MDI | Isofol-14T | | 3/2 |
| HCD-9 | MDI | Isofol-16 | | 3/2 |
| HCD-10 | MDI | Isofol-18T | | 3/2 |
| HCD-11 | MDI | Isofol-18T | | 2/1 |
| HCD-12 | MDI | Isofol-20 | | 3/2 |
| HCD-13 | MDI | Isofol-24 | | 3/2 |
| HCD-14 | MDI | 2-Ethylhexanol | | 3/2 |
| HCD-15 | TDI | Guerbitol-18 | | 2/1 |
| HCD-16 | Voranate M220 | Prisorine 3515 | | 3/5 |
| HCD-17 | MDI | Guerbitol-18 | Jeffamine 715 | 3/1.8/0.2 |
| HCD-18 | MDI | Guerbitol-18 | MPEG 750 | 3/1.8/0.2 |
| HCD-19 | MDI | Guerbitol-18 | DEAE | 3/1.8/0.2 |
| HCD-20 | MDI | Guerbitol-18 | MPEG 750 | 3/1.9/0.1 |
| HCD-21 | MDI | Guerbitol-18 | MPEG 750/DEAE | 3/1.8/0.1/0.1 |
| HCD-22 | MDI | Isofol-18T | MPEG 350 | 3/1.9/0.1 |
| HCD-23 | MDI | Isofol-18T | MPEG 350 | 3/1.8/0.2 |
| HCD-24 | MDI | Isofol-18T | MPEG 350 | 4/1.9/0.1 |
| HCD-25 | MDI | Isofol-18T | MPEG 350 | 4/1.8/0.2 |

It has been found that the use of ammonium surfactants having two long chain alkyl groups or mixtures of said ammonium surfactants and nonionic surfactants afford increased emulsion stability, especially when hard water is used to dilute the emulsion.

Ammonium surfactants having two long chain alkyl groups can be represented by the general formula

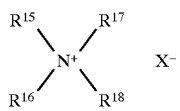

wherein:
—$R^{15}$ and $R^{16}$ each and independently are long chain alkyl groups containing at least eight carbon atoms, preferably from 8 to 24 carbon atoms or benzyl and —$R^{17}$ and $R^{18}$ each and independently are short chain alkyl groups having from 1 to 8 carbon atoms or hydrogen. X can be halogen (Cl—, Br—, I—)$HSO_4$—$CH_3$—COO—.

The use of ammonium surfactants having two long chain alkyl groups increases emulsion stability, without sacrifice of the properties of the treated substrate. It seems that the same effects are observed not only for carbodiimide emulsions but in general for hydrocarbon and fluorochemical emulsions.

Synthesis of the fluorochemical carbodiimide (FCD) used in comparative examples C-2 to C-8, C-10, C-12, C-14 and C-16

The fluorochemical carbodiimide FCD, used in comparative examples C-2 to C-8, C-10, C-12, C-14 and C-16 has been prepared according to example 2 in U.S. Pat. No. 4,024,178, with the exception that MDI was used instead of toluene diisocyanate (TDI) and the molar ratio of fluorochemical/isocyanate was 2/3 instead of 1/3.

Fluorochemical agents

Several of the fluorochemical treating agents used in the examples of the present invention are commercially available from Minnesota Mining and Manufacturing Company, others have been prepared:

Commercially available fluorochemical treating agents

FC 3531 is a weakly cationic fluorochemical emulsion polymer

FC 461 is a nonionic fluorochemical emulsion polymer

FX 889 is a cationic fluorochemical emulsion polymer

FC 217 is a cationic fluorochemical emulsion polymer

Experimental fluorochemical treating agents

The experimental fluorochemical agents that are used in the examples are made according to the procedure described below for the synthesis of MEFOSEA/EHMA 80/20.

A polymerization bottle was charged with 150 g N-methylperfluorooctylsulfonamidoethyl acrylate (MEFOSEA), 37.5 g 2-ethylhexyl methacrylate, 9.4 g Ethoquad TM 18/25, 1.4 g n-octylmercaptan, 0.94 g V-50 TM initiator (2,2'-azobis(2-methylpropionamidine) dihydrochloride, available from Wacko, Osaka, Japan), 109 g acetone and 434 g deionized water. The reaction mixture was deaerated and covered with a nitrogen atmosphere. The polymerization bottle was capped and run in a Launder-o-meter at 73° C. for 16 hours. Acetone was removed from the resulting transparent dispersion via vacuum distillation.

Table 2 lists the weight ratio of the raw materials used in the preparation of the fluorochemical polymer emulsions that are used in combination with hydrocarbon carbodiimides.

TABLE 2

Experimental fluorochemical agents

|  | MEFOSEMA | MEFOSEA | EHMA | N-MAM |
|---|---|---|---|---|
| FC-1 | 80 |  | 20 |  |
| FC-2 | 80 |  | 17 | 3 |
| FC-3 |  | 80 | 20 |  |
| FC-4 |  | 80 | 17 | 3 |

Examples 1 to 7 and comparative examples C-1 to C-10

In Examples 1 to 7, blends were made of FC-3531 fluorochemical with hydrocarbon carbodiimide HCD-1 in different ratio's as given in table 3. The blends were applied to PES/CO fabric as outlined in the general treatment procedure. Comparative example C-1 only contains fluorochemical treatment agent FC-3531; comparative examples C-2 to C-8 were made using a blend of FC-3531 and fluorochemical carbodiimide FCD comparative examples C-9 and C-10 are made with the hydrocarbon and fluorocarbon carbodiimides (HCD-1 and FCD) respectively, but without addition of FC-3531.

The performance results are given in table 3.

TABLE 3

Performance properties of PES/CO fabric treated with FC-353 1/carbodiimide mixtures (0.3% SOF)

| Ex. | Carbo-diimide | Ratio of FX-3531/ Carbodi-imide | Bundesmann 1 min | 5 min | 10 min | % ABS | OR Init. | 5L | SR Init. | 5L |
|---|---|---|---|---|---|---|---|---|---|---|
| C-1 | / | 100/0 | 5 | 3 | 2 | 17 | 4 | 4 | 100 | 80 |
| 1 | HCD-1 | 90/10 | 5 | 4 | 3 | 18 | 5 | 4 | 100 | 90 |
| C-2 | FCD | 90/10 | 4 | 3 | 2 | 14 | 4 | 4 | 100 | 80 |
| 2 | HCD-1 | 80/20 | 5 | 4 | 3 | 16 | 5 | 4 | 100 | 100 |
| C-3 | FCD | 80/20 | 3 | 2 | 1 | 19 | 4 | 4 | 100 | 80 |
| 3 | HCD-1 | 70/30 | 5 | 4 | 3 | 15 | 5 | 4 | 100 | 90 |
| CA | FCD | 70/30 | 3 | 1 | 1 | 19 | 5 | 4 | 100 | 80 |
| 4 | HCD-1 | 60/40 | 5 | 4 | 3 | 15 | 5 | 4 | 100 | 90 |
| C-5 | FCD | 6O/40 | 2 | 1 | 1 | 20 | 5 | 4 | 100 | 80 |
| 5 | HCD-1 | 50/50 | 5 | 4 | 2 | 19 | 4 | 4 | 100 | 90 |
| C-6 | FCD | 50/10 | 2 | 1 | 1 | 21 | 5 | 4 | 100 | 80 |
| 6 | HCD-I | 40/60 | 5 | 4 | 2 | 20 | 4 | 3 | 100 | 90 |
| C-7 | FCD | 40/60 | 2 | 1 | 1 | 22 | 5 | 4 | 100 | 80 |
| 7 | HCD-I | 30/70 | 4 | 2 | 1 | 20 | 3 | 2 | 100 | 90 |
| C-8 | FCD | 30/70 | 2 | 1 | 1 | 20 | 5 | 3 | 100 | 80 |
| C-9 | HCD-1 | 0/100 | 1 | 1 | 1 | 40 | 0 | 0 | 70 | 50 |
| C-10 | FCD | 0/100 | 1 | 1 | 1 | 23 | 5 | 3 | 100 | 70 |

TABLE 4

Cumulative Bundesmann results of PESICO fabric treated with FC-3531/carbodiimide mixtures

| Ex. No. | Carbo-diimide | FC-3531/Carbod. Ratio | Fluorine Content* | Cumulative Bundesmann** |
|---|---|---|---|---|
| C-1 | / | 100/1 | 3.8 | 10 |
| 2 | HCD-1 | 80/20 | 19.0 | 12 |
| C-3 | FCD | 80/20 | 26.0 | 6 |
| 4 | HCD-1 | 60/40 | 14.3 | 12 |
| C-5 | FCD | 60/40 | 28.3 | 4 |
| 6 | HCD-1 | 40/60 | 9.5 | 11 |
| C-7 | FCD | 40/60 | 30.5 | 4 |
| C-9 | HCD-1 | 0/100 | 0 | 3 |
| C-10 | FCD | 0/100 | 35.0 | 3 |

Note:
*fluorine content is given as weight % organically bonded fluorine
**Cumulative Bundesmann is the sum of the visual ratings after 1, 5 and 10 min.

The results given in table 4 clearly demonstrate that, despite the lower fluorine content, the treatment solutions comprising fluorochemical agent and hydrocarbon carbodi-imide outperform the solutions containing only fluorochemical or a combination of fluorochemical and fluorocarbodiimide.

Examples 8 to 10 and comparative examples C-11 to C-16

In examples 8 to 10 a treatment solution containing fluorochemical agent FC-3531 and hydrocarbon carbodiimide HCD-1 in a ratio of 60/40 by weight was used to treat substrates as cotton, polyester (PES) and polyamide (PA) microfibers. Comparative examples C-11, C-13 and C-15 were made without addition of carbodiimide and comparative examples C-12, C-14 and C-16 were made with a mixture of FC-3531 and fluorocarbon carbodiimide FCD in a ratio of 60/40. The results of oil and water repellency of the treated fabrics are given in table 5.

The results of the experiments shown in this table indicate that improvement in overall repellency is obtained, even when small amounts (10%) of fluorochemical FC-3531 are replaced by hydrocarbon carbodiimide. A 40/60 mixture of FC-3531 with hydrocarbon carbodiimide still gives comparable results as the fluorochemical treatment alone. Compared to fluorocarbodiimide, overall better performance is obtained with the hydrocarbon carbodiimides. This is remarkable, especially if the fluorine content of the treatment composition is considered. In table 4, the cumulative Bundesmann ratings are given as a function of the fluorine content of the treatment solutions.

TABLE 5

Performance properties of fabrics treated with FC-3531/carbodiimide 60/40 mixtures (0.3% SOF)

| Ex. No. | Carbod. | Substrate | Bundesmann | | | | OR | | SR | |
|---|---|---|---|---|---|---|---|---|---|---|
| | | | 1 min | 5 min | 10 min | % ABS | Init. | 5L | Init. | 5L |
| 8 | HCD-1 | Cotton | 4 | 2 | 1 | 25 | 4 | 5 | 100 | 90 |
| C-11 | / | Cotton | 1 | 1 | 1 | 29 | 4 | 3 | 100 | 70 |
| C-12 | FCD | Cotton | 1 | 1 | 1 | 32 | 4 | 4 | 80 | 70 |
| 9 | HCD-1 | PES | 5 | 5 | 5 | 5 | 3 | 2 | 100 | 90 |
| C-13 | / | PES | 5 | 5 | 5 | 4 | 2 | 2 | 100 | 70 |
| C-14 | FCD | PES | 3 | 1 | 1 | 21 | 3 | 2 | 100 | 90 |
| 10 | HCD-1 | PA | 5 | 5 | 4 | 10 | 3 | 2 | 100 | 90 |
| C-15 | / | PA | 5 | 4 | 3 | 27 | 4 | 0 | 100 | 60 |
| C-16 | FCD | PA | 3 | 3 | 1 | 26 | 3 | 1 | 100 | 80 |

Examples 11 to 16 and Comparative examples C-17 to C-22

In examples 11 to 16 treatment solutions of different commercially available fluorochemical treatment agents and hydrocarbon carbodiimide HCD-1, in a ratio of 60/40, were applied to polyester/cotton and to polyamide microfibers. Comparative examples C-17 to C-22 were made without addition of carbodiimide. The results of oil and water repellency, also after dry cleaning (DC), of the treated substrates are in table 6.

Examples 17 to 24 and comparative examples C-23 to C-30

The same experiment was repeated with experimental fluorochemical agents. The composition of the fluorochemical treating agents is given in table 2. Examples 17 to 24 were made by treating polyester/cotton and polyamide microfiber with a blend of fluorochemical agent and hydrocarbon carbodiimide in a ratio of 50/50 by padding in order to provide a concentration of 0.4% SOF. The hydrocarbon carbodiimide used was made from MDI and Guerbitol-20 in

TABLE 6

Performance properties of substrates treated with a 60/40 blend of fluorochemical agent and carbodiimide (0.3% SOF)

| Ex. No. | Fluoro-chemical | Carbo-diimide | Bundesmann | | | | OR | | | SR | | |
|---|---|---|---|---|---|---|---|---|---|---|---|---|
| | | | 1 min | 5 min | 10 min | % ABS | Init. | 5L | DC | Init. | 5L | DC |
| Polyester/cotton substrate | | | | | | | | | | | | |
| 11 | FC-461 | HCD-1 | 2 | 1 | 1 | 25 | 4 | 3 | 4 | 90 | 60 | 70 |
| C-17 | FC-461 | / | 1 | 1 | 1 | 33 | 6 | 5 | 3 | 100 | 60 | 50 |
| 12 | FX-889 | HCD-1 | 5 | 4 | 3 | 12 | 6 | 5 | 4 | 100 | 80 | 60 |
| C-18 | FX-889 | 1 | 2 | 1 | 1 | 21 | 5 | 4 | 4 | 100 | 60 | 60 |
| 13 | FC-217 | HCD-1 | 1 | 1 | 1 | 26 | 5 | 4 | 3 | 70 | 60 | 50 |
| C-19 | FC-217 | / | 1 | 1 | 1 | 34 | 5 | 4 | 3 | 70 | 50 | 50 |
| Polyamide microfiber | | | | | | | | | | | | |
| 14 | FC-461 | HCD-1 | 5 | 5 | 5 | 9 | 4 | 2 | 1 | 100 | 90 | 90 |
| C-20 | FC-461 | / | 5 | 1 | 1 | 23 | 5 | 0 | 3 | 100 | 50 | 70 |
| 15 | FX-889 | HCD-1 | 5 | 5 | 5 | 10 | 5 | 2 | 2 | 100 | 80 | 80 |
| C-21 | FX-889 | / | 1 | 5 | 5 | 5 | 12 | 4 | 3 | 100 | 50 | 80 |
| 16 | FC-217 | HCD-1 | 3 | 2 | 2 | 35 | 5 | 2 | 3 | 90 | 80 | 80 |
| C-22 | FC-217 | / | 2 | 1 | 1 | 47 | 6 | 1 | 3 | 80 | 50 | 80 |

Not only on cotton fabrics, but also on synthetic substrates, very high performance is obtained. A replacement of 40% of the fluorochemical treating agent with carbodiimide does not harm the water repellency of the treated fabric; in many cases better performance is observed.

a ratio 2/1 (same as hydrocarbon carbodiimide HCD-7 in table 1). Comparative examples C-23 to C-30 were made with fluorochemical treating agent, but without carbodiimide. The results of oil and water repellency are given in table 7.

TABLE 7

Performance properties of substrates treated with fluorochemical treating agents and carbodiimide HCD-7 (0.4% SOF)

| Ex. No. | Fluoro-chemical | Ratio FC/HCD | Bundesmann 1' | 5' | 10' | % ABS | OR Init. | 5L | SR Init. | 5L |
|---|---|---|---|---|---|---|---|---|---|---|
| Polyester/cotton substrate | | | | | | | | | | |
| 17 | FC-1 | 50/50 | 5 | 4 | 3 | 12 | 3 | 3 | 100 | 80 |
| C-23 | FC-1 | 100/0 | 1 | 1 | 1 | 35 | 4 | 1 | 90 | 0 |
| 18 | FC-2 | 50/50 | 5 | 4 | 3 | 10 | 4 | 2 | 100 | 80 |
| C-24 | FC-2 | 100/0 | 2 | 1 | 1 | 25 | 4 | 2 | 90 | 50 |
| 19 | FC-3 | 50/50 | 5 | 5 | 4 | 9 | 6 | 5 | 100 | 80 |
| C-25 | FC-3 | 100/0 | 1 | 1 | 1 | 33 | 6 | 3 | 90 | 0 |
| 20 | FCA | 50/50 | 5 | 5 | 4 | 14 | 6 | 4 | 100 | 80 |
| C-26 | FC-4 | 100/0 | 2 | 1 | 1 | 27 | 6 | 5 | 90 | 50 |
| Polyamide microfiber | | | | | | | | | | |
| 21 | FC-1 | 50/50 | 5 | 5 | 5 | 10 | 4 | 2 | 100 | 100 |
| C-27 | FC-1 | 100/0 | 4 | 3 | 3 | 29 | 2 | 0 | 100 | 0 |
| 22 | FC-2 | 50/50 | 5 | 5 | 4 | 9 | 3 | 2 | 100 | 90 |
| C-28 | FC-2 | 100/0 | 4 | 3 | 2 | 34 | 2 | 0 | 100 | 50 |
| 23 | FC-3 | 50/50 | 5 | 5 | 5 | 11 | 6 | 4 | 100 | 80 |
| C-29 | FC-3 | 100/0 | 5 | 4 | 3 | 19 | 4 | 0 | 100 | 0 |
| 24 | FC-4 | 50/50 | 5 | 4 | 3 | 13 | 5 | 3 | 100 | 80 |
| C-30 | FC-4 | 100/0 | 5 | 4 | 3 | 17 | 5 | 1 | 90 | 50 |

Examples 25 to 51 and comparative examples C-31 and C-32

The influence of the structure of the hydrocarbon carbodiimide was evaluated in examples 25 to 51. The carbodiimides evaluated were based on different isocyanates and various alcohols as indicated in table 1. Blends of FC-3531 fluorochemical with the hydrocarbon carbodiimides (ratio 60/40) were applied to polyester/cotton fiber and to polyamide microfiber. Comparative examples C-31 and C-32 were made without addition of hydrocarbon carbodiimide. The results of oil and water repellency are given in table 8.

TABLE 8

Performance properties of substrates treated with blends of FC-3531 with hydrocarbon carbodiimides (0.3% SOF)

| Ex. No. | Hydrocarbon Carbodiimide | Bundesmann 1 min | 5 min | 10 min | % ABS | OR Init. | 5L | SR Init. | 5L |
|---|---|---|---|---|---|---|---|---|---|
| Polyester/cotton substrate | | | | | | | | | |
| 25 | HCD-2 | 4 | 4 | 3 | 14 | 5 | 5 | 100 | 90 |
| 26 | HCD-3 | 5 | 54 | 3 | 15 | 5 | 5 | 100 | 80 |
| 27 | HCD-4 | 5 | 4 | 3 | 15 | 5 | 5 | 100 | 70 |
| 28 | HCD-5 | 4 | 4 | 3 | 14 | 5 | 5 | 100 | 90 |
| 29 | HCD-6 | 5 | 4 | 2 | 17 | 5 | 5 | 100 | 80 |
| 30 | HCD-7 | 5 | 4 | 3 | 10 | 5 | 5 | 100 | 80 |
| 31 | HCD-8 | 4 | 3 | 2 | 21 | 5 | 5 | 100 | 60 |
| 32 | HCD-9 | 5 | 4 | 3 | 18 | 5 | 5 | 100 | 80 |
| 33 | HCD-10 | 5 | 4 | 2 | 17 | 5 | 5 | 100 | 80 |
| 34 | HCD-12 | 5 | 3 | 2 | 15 | 5 | 5 | 100 | 70 |
| 35 | HCD-13 | 5 | 4 | 2 | 20 | 5 | 5 | 100 | 80 |
| 36 | HCD-14 | 5 | 4 | 3 | 17 | 2 | 2 | 100 | 80 |
| 37 | HCD-15 | 5 | 4 | 2 | 20 | 5 | 5 | 100 | 80 |
| 38 | HCD-16 | 5 | 3 | 2 | 22 | 5 | 5 | 100 | 70 |
| C-31 | / | 5 | 3 | 1 | 24 | 5 | 3 | 100 | 60 |
| Polyamide microfiber | | | | | | | | | |
| 39 | HCD-2 | 5 | 5 | 5 | 5 | 5 | 4 | 100 | 90 |
| 40 | HCD-3 | 5 | 5 | 4 | 10 | 5 | 5 | 100 | 80 |
| 41 | HCD-4 | 5 | 5 | 5 | 9 | 5 | 5 | 100 | 80 |
| 42 | HCD-5 | 5 | 5 | 5 | 7 | 5 | 4 | 100 | 90 |
| 43 | HCD-6 | 5 | 5 | 4 | 14 | 5 | 5 | 100 | 80 |
| 44 | HCD-7 | 5 | 5 | 5 | 7 | 5 | 4 | 100 | 90 |
| 45 | HCD-8 | 5 | 4 | 4 | 13 | 4 | 5 | 100 | 60 |
| 46 | HCD-9 | 5 | 5 | 5 | 11 | 5 | 5 | 100 | 80 |
| 47 | HCD-10 | 5 | 5 | 4 | 13 | 5 | 5 | 100 | 70 |
| 48 | HCD-12 | 5 | 5 | 4 | 11 | 5 | 5 | 100 | 80 |
| 49 | HCD-13 | 5 | 4 | 4 | 13 | 5 | 5 | 100 | 80 |

TABLE 8-continued

Performance properties of substrates treated with blends of FC-3531 with hydrocarbon carbodiimides (0.3% SOF)

| Ex. No. | Hydrocarbon Carbodiimide | Bundesmann 1 min | 5 min | 10 min | % ABS | OR Init. | 5L | SR Init. | 5L |
|---|---|---|---|---|---|---|---|---|---|
| 50 | HCD-15 | 5 | 5 | 5 | 11 | 5 | 3 | 100 | 80 |
| 51 | HCD-16 | 5 | 5 | 5 | 11 | 5 | 5 | 100 | 60 |
| C-32 | / | 5 | 4 | 3 | 14 | 4 | 3 | 100 | 50 |

In both experiments it becomes clear that the hydrocarbon carbodimides improve the overall water and oil repellency of the treated fabrics, both of cellulose type fabrics and synthetic fabrics.

Examples 52 to 63

Examples 52 to 63 were made to illustrate that the disclosed carbodiimides can be emulsified using a variety of surfactants or mixtures of surfactants. The carbodiimide evaluated was made from MDI/Isofol 18T (2/1; same as HCD-11 in table 1). The carbodiimide was emulsified according to the general procedure. The kind and the level of surfactants evaluated are given in table 9. The carbodiimide emulsion was blended with fluorochemical treating agent FC-3531 at a ratio of 60/40 FC/HCD. Polyester/cotton and polyamide fibers were treated with this mixture at 0.3% SOF and cured for 3 minutes at 150° C. The results of oil and water repellency and durability are given in table 9.

Examples 64 to 73

Examples 64 to 73 were done in order to evaluate the performance of compositions comprising fluorochemical treating agent and hydrocarbon carbodiimide containing emulsion aids. The carbodiimide emulsions from examples 64 and 69 were prepared according to the general method (10% surfactant based on hydrocarbon carbodiimide solids); the carbodiimide emulsions from examples 65, 67, 68, 70 and 72 to 73 contain only 5% surfactant and the emulsions from example 66 and 71 do not contain any emulsifier at all. Blends of FC-3531 with the hydrocarbon carbodiimides (ratio 60/40) were applied to polyester/cotton and to polyamide microfiber. The results of oil and water repellency are given in table 10.

TABLE 9

Performance properties of fabrics treated with FC-3531/hydrocarbon carbodiimide HCD-11 (60/40 0.3% SOF) using various surfactants

| Ex. No. | Surfactant | (%) Surf. | Bundesmann 1 min. | 5 min. | 10 min. | % ABS | OR Init. | 5L | SR Init. | 5L |
|---|---|---|---|---|---|---|---|---|---|---|
| Polyester/cotton substrate | | | | | | | | | | |
| 52 | Marlowet 5401 | 5 | 5 | 3 | 2 | 17 | 5 | 4 | 100 | 80 |
| 53 | Ethoquad HT-25 | 5 | 5 | 4 | 3 | 16 | 5 | 4 | 100 | 90 |
| 54 | Arquad T-50 | 5 | 5 | 3 | 3 | 13 | 5 | 4 | 100 | 80 |
| 55 | Arquad 2HT-75 | 5 | 5 | 5 | 3 | 11 | 5 | 4 | 100 | 90 |
| 56 | Arquad 2HT-75 + Atpol E5721 | 4 4 | 5 | 4 | 3 | 13 | 5 | 3 | 100 | 90 |
| 57 | Arquad 2HT-75 + Atlas G1281 | 4 4 | 5 | 5 | 4 | 12 | 5 | 4 | 100 | 90 |
| Polyamide substrate | | | | | | | | | | |
| 58 | Marlowet 5401 | 5 | 5 | 4 | 4 | 14 | 5 | 4 | 100 | 80 |
| 59 | Ethoquad HT-25 | 5 | 5 | 5 | 4 | 13 | 5 | 4 | 100 | 90 |
| 60 | Arquad T-50 | 5 | 5 | 3 | 2 | 26 | 5 | 4 | 100 | 80 |
| 61 | Arquad 2HT-75 | 5 | 5 | 5 | 5 | 7 | 5 | 4 | 100 | 90 |
| 62 | Arquad 2HT-75 + Atpol E5721 | 4 4 | 5 | 5 | 5 | 6 | 5 | 3 | 100 | 90 |
| 63 | Arquad 2HT-75 + Atlas G1281 | 4 4 | 5 | 5 | 5 | 12 | 5 | 4 | 100 | 90 |

Examples 52–63 illustrate that the disclosed carbodiimides can be emulsified using a variety of surfactants or a mixture of surfactants. In particular, examples 55 to 57 and 61 to 63, show that substrates, treated with compositions emulsified with ammonium surfactants having two long chain alkyl groups, show high overall performance.

TABLE 10

Performance properties of substrates treated with blends of FC-3531 and hydrocarbon carbodiimide (0.3% SOF)

| Ex. No. | Hydrocarbon Carbodiimide | % Surfact. | Bundesmann 1' | 5' | 10' | % ABS | OR Init. | 5L | SR Init. | 5L |
|---|---|---|---|---|---|---|---|---|---|---|
| Polyester/cotton substrate | | | | | | | | | | |
| 64 | HCD-18 | 10 | 5 | 3 | 2 | 17 | 5 | 4 | 100 | 70 |
| 65 | HCD-18 | 5 | 5 | 3 | 2 | 18 | 5 | 4 | 100 | 80 |
| 66 | HCD-18 | 0 | 4 | 2 | 1 | 21 | 5 | 3 | 100 | 70 |
| 67 | HCD-19 | 5 | 4 | 3 | 2 | 18 | 5 | 4 | 100 | 80 |
| 68 | HCD-21 | 5 | 5 | 4 | 2 | 17 | 5 | 4 | 100 | 80 |
| Polyamide microfiber | | | | | | | | | | |
| 69 | HCD-18 | 10 | 5 | 4 | 4 | 18 | 4 | 3 | 100 | 80 |
| 70 | HCD-18 | 5 | 3 | 2 | 1 | 31 | 4 | 3 | 90 | 80 |
| 71 | HCD-18 | 0 | 4 | 2 | 2 | 33 | 4 | 2 | 100 | 80 |
| 72 | HCD-19 | 5 | 5 | 5 | 5 | 10 | 4 | 3 | 100 | 90 |
| 73 | HCD-21 | 5 | 5 | 5 | 5 | 19 | 4 | 3 | 100 | 90 |

Examples 74 to 77 and comparative examples C-33 to C-36

Following experiment is done in order to illustrate the influence of the addition of resins to the fluorochemical/carbodiimide treatment formulations. Examples 74 and 76 were made by treating cotton and polyester/cotton with a blend containing fluorochemical agent FC-3531, hydrocarbon carbodiimide HCD-1 (ratio 60/40 FC/HCD-1), Reaknitt DFL (a carbamid resin, available from CHT R. Beitlich GmbH, Tuebingen, Germany) and CHT-catalyst (available from CHT R. Beitlich, Tuebingen, Germany). The resin was added to the treatment solution containing fluorochemical agent and hydrocarbon carbodiimide at a concentration of 50 g/l. The catalyst was added at a concentration of 5 g/l. The treated substrates were cured at 150° C. for 3 min. The performance of the treated substrates was compared to substrates treated with a mixture of FC-3531 and HCD-1 (examples 75 and 77) and to substrates treated with only FC-3531 (Comparative examples C-33 and C-35) or with a mixture of FC-3531 and resin (C-34 and C-36). The results of oil and water repellency test are given in table 11.

The results of this test show that the dynamic water repellency and the durability of the treatment can further be improved by adding a carbamid resin to the solution of fluorochemical treating agent and hydrocarbon carbodiimide. Compared to the samples without hydrocarbon carbodiimide, the improvement in properties is considerable.

We claim:

1. A water repellant composition comprising at least one essentially fluorine-free carbodiimide compound obtainable from a reaction mixture comprising an isocyanate compound and a monofunctional alcohol in a non-reactive solvent in the presence of a suitable catalyst, characterized in that the isocyanate compound and the monofunctional alcohol, except for the hydroxy group, are free from isocyanate reactive hydrogen atoms and the monofunctional alcohol is a branched aliphatic alcohol containing at least 8 carbon atoms; and at least one fluorochemical compound.

2. The composition according to claim 1 wherein the fluorochemical compound is a copolymer of at least one monomer represented by the general formula

TABLE 11

Performance properties of substrates treated with blends of FC-3531/hydrocarbon carbodiimide/resin (0.3% SOF)

| Ex. No. | FC-3531 | HCD-1 | Resin | Bundesmann 1 min | 5 min | 10 min | % ABS | OR Init. | 5L | SR Init. | 5L |
|---|---|---|---|---|---|---|---|---|---|---|---|
| Cotton Substrate | | | | | | | | | | | |
| 74 | x | x | x | 5 | 3 | 2 | 21 | 3 | 3 | 100 | 90 |
| 75 | x | x | | | | | | 3 | 2 | 100 | 80 |
| C-33 | x | | | | | | | 2 | 1 | 90 | 50 |
| C-34 | x | | x | 2 | 1 | 1 | 41 | 2 | 2 | 90 | 70 |
| Polyester/cotton | | | | | | | | | | | |
| 76 | x | x | x | 5 | 4 | 3 | 14 | 6 | 4 | 100 | 100 |
| 77 | x | x | | 5 | 3 | 2 | 17 | 5 | 4 | 100 | 80 |
| C-35 | x | | | 4 | 3 | 2 | 19 | 5 | 4 | 100 | 70 |
| C-36 | x | | x | 5 | 4 | 3 | 12 | 6 | 5 | 100 | 90 |

$R_fR^1OCOC(R^2)=CH_2$ and $R_fSO_2N(R^3)R^4OCOC(R^2)=CH_2$ in which $R_f$ is a fluoroaliphatic radical having at least 3 carbon atoms which can contain heteroatoms selected from O, S and N;

$R^1$ is an alkylene with 1 to 10 carbon atoms, or —$CH_2CH(OR)CH_2$—, in which R is hydrogen or $COCH_3$;

$R^2$ is hydrogen or methyl;

$R^3$ is hydrogen or an alkyl with 1 to 20 carbon atoms; and $R^4$ is an alkylene with 1 to 20 carbon atoms and at least one fluorine-free terminally ethylenically unsaturated comonomer.

3. The composition of claim 2 in which the fluorochemical compound is a copolymer of a fluorinated monomer selected from N-methyl perfluorooctylsulfon-amidoethyl acrylate $C_8F_{17}SO_2N(CH_3)CH_2CH_2OC(O)CH=CH_2$ and N-methyl perfluorooctylsulfonamidoethyl methacrylate and a terminally ethylenically unsaturated monomer selected from ethyl-hexylmethacrylate.

4. The composition of claim 2 in which there are 25–200 parts by weight carbodiimide per 100 parts by weight of fluorochemical compound.

5. A method for treating a substrate selected from the group consisting of woven textile fabrics, fibers, nonwovens, leather, paper, carpet, plastic, wood, metal, glass, concrete and stone to impart oil and water repellency comprising applying to the substrate a composition of claim 1.

6. The method of claim 5 in which the substrate is selected from the group consisting of rayon, cotton, linen and other cellulosic substrates.

7. The combination of substrate and a water repellent composition selected from the compositions of claim 1 and the same compositions which have been cured on the substrate.

8. A dispersion comprising water; at least one essentially fluorine-free carbodiimide compound obtainable from a reaction mixture comprising an isocyanate compound and a monofunctional alcohol in a non-reactive solvent in the presence of a suitable catalyst, characterized in that the isocyanate compound and the monofunctional alcohol, except for the hydroxy group, are free from isocyanate reactive hydrogen atoms and the monofunctional alcohol is a branched aliphatic alcohol containing at least 8 carbon atoms; and at least one fluorochemical compound; which dispersion is effective to provide repellent properties to a substrate treated therewith and contains a surfactant in an amount effective to stabilize the dispersion.

9. Dispersion according to claim 8 in which water is present in an amount of 70 to 20,000 parts-by-weight based on 100 parts-by-weight of the combined weights of carbodiimide and fluorochemical compounds, and the surfactant is present in an amount up to 25 parts-by-weight on the same weight basis.

* * * * *